US009466012B2

(12) United States Patent
Ritt et al.

(10) Patent No.: US 9,466,012 B2
(45) Date of Patent: Oct. 11, 2016

(54) PHANTOM IMAGE CLASSIFICATION (71) Applicant: Radiological Imaging Technology, Inc., Colorado Springs, CO (US)

(72) Inventors: Daniel M. Ritt, Colorado Springs, CO (US); Logan Flewellen, Colorado Springs, CO (US); Matthew L. Whitaker, Colorado Springs, CO (US); Ryan Young, Colorado Springs, CO (US)

(73) Assignee: Radiological Imaging Technology, Inc., Colorado Springs, CO (US)

( * ) Notice: Subject to any disclaimer, the term of this patent is extended or adjusted under 35 U.S.C. 154(b) by 382 days.

(21) Appl. No.: 13/952,003

(22) Filed: Jul. 26, 2013

(65) Prior Publication Data

US 2015/0016699 A1    Jan. 15, 2015

Related U.S. Application Data

(60) Provisional application No. 61/845,283, filed on Jul. 11, 2013.

(51) Int. Cl.
*G06K 9/62* (2006.01)
*A61B 6/00* (2006.01)
*G06F 17/30* (2006.01)
*A61B 17/00* (2006.01)
*G06F 19/00* (2011.01)

(52) U.S. Cl.
CPC .......... *G06K 9/6262* (2013.01); *G06K 9/6227* (2013.01); *G06K 9/6282* (2013.01); *A61B 6/583* (2013.01); *A61B 2017/00712* (2013.01); *G06F 17/30* (2013.01); *G06F 19/321* (2013.01); *G06K 2209/05* (2013.01); *G06K 2209/27* (2013.01)

(58) Field of Classification Search
CPC ............ G06K 9/6227; G06K 9/6262; G06K 9/6282; G06K 19/06; G06K 2209/05; G06K 2209/27; G06F 17/30; G06F 19/321; A61B 5/0035; A61B 6/4417; A61B 6/583; A61B 2017/00712; A61B 2017/00716; G01R 33/58
See application file for complete search history.

(56) References Cited

U.S. PATENT DOCUMENTS 5,841,835 A    11/1998  Aufrichtig et al.
5,994,900 A    11/1999  Gurvich
6,115,489 A *   9/2000  Gupta ................... G06F 19/321
                                                        382/141

(Continued)

OTHER PUBLICATIONS

D.J. Withey et al., "Medical Image Segmentation: Methods and Software", Proceedings of NFSI & ICFBI 2007, Hangzhou China, Oct. 12-14, 2007, pp. 140-143.

(Continued)

*Primary Examiner* — Katrina Fujita
(74) *Attorney, Agent, or Firm* — Bejin Bieneman PLC (57) ABSTRACT

A computing device uses image metadata to perform a first sub-classification of an image, wherein the first sub-classification is deterministic, then uses a combination of image data and the image metadata to perform a second sub-classification, further in a third sub-classification, uses image data to make a probabilistic classification of an image according to a likely phantom type. Alternatively or additionally, a computing device receives a set of image analysis data, identifies an image analysis model to be trained, using the image analysis data, determines that the image analysis model can include an image permutation, and trains a new image analysis model including the image permutation.

19 Claims, 8 Drawing Sheets

(56) References Cited

U.S. PATENT DOCUMENTS

| | | | |
|---|---|---|---|
| 6,501,849 B1* | 12/2002 | Gupta | G06F 19/321 |
| | | | 382/141 |
| 6,694,047 B1* | 2/2004 | Farrokhnia | A61B 6/583 |
| | | | 378/163 |
| 7,729,524 B2 | 6/2010 | Rogers et al. | |
| 7,783,094 B2 | 8/2010 | Collins et al. | |
| 7,983,732 B2 | 7/2011 | Chen et al. | |
| 7,995,822 B2 | 8/2011 | Lang et al. | |
| 8,031,836 B2 | 10/2011 | Lang et al. | |
| 8,050,503 B2* | 11/2011 | Dekel et al. | 382/209 |
| 8,131,036 B2 | 3/2012 | Collins et al. | |
| 8,308,362 B2 | 11/2012 | Dove et al. | |
| 8,357,094 B2 | 1/2013 | Mo et al. | |
| 2004/0147840 A1 | 7/2004 | Duggirala et al. | |
| 2006/0280348 A1* | 12/2006 | Smith et al. | 382/128 |
| 2008/0005746 A1* | 1/2008 | Jianzhong | G06F 9/4843 |
| | | | 719/315 |
| 2008/0114242 A1* | 5/2008 | Chang | A61B 8/08 |
| | | | 600/443 |
| 2009/0052631 A1 | 2/2009 | Cresens et al. | |
| 2010/0260396 A1 | 10/2010 | Brandt et al. | |
| 2011/0188715 A1 | 8/2011 | Shotton et al. | |
| 2012/0076371 A1* | 3/2012 | Caruba | A61B 6/583 |
| | | | 382/128 |
| 2012/0177270 A1 | 7/2012 | Bao et al. | |

OTHER PUBLICATIONS

E. Schreibmann et al., "Automated Quality Assurance for Image-Guided Radiation Therapy", Journal of Applied Clinical Medical Physics, vol. 10, No. 1, Winter 2009, 11 pages.

W.H. Chao et al., "Automatic segmentation of magnetic resonance images using a decision tree with spatial information", Computerized Medical Imaging and Graphics 33 (2008), pp. 111-121.

* cited by examiner

Original ACR CT phantom Slice 4 image. 512x512

Preprocessing crops the phantom image to the inner bounds of the phantom.

Preprocessed image is sub-sampled down to 32x32.

Each pixel in sub-sampled image is used as an input to the percepton.

PHANTOM IMAGE CLASSIFICATION

RELATED APPLICATION

This application claims priority to U.S. Provisional Patent Application No. 61/845,283, entitled "PHANTOM IMAGE CLASSIFICATION," filed Jul. 11, 2013, the contents of which are fully incorporated herein by reference in their entirety.

BACKGROUND

Currently, the user of a medical imaging quality assurance (QA) software system is required to explicitly specify a type of QA phantom used to generate the image being loaded into the software system before the analysis of the image can begin. Additionally, a novice user may not know, or may be unsure, of the proper form of analysis to be applied to an image. Thus, a user must often select a form of analysis is to be conducted on an image from a large list of possibilities. While a user may have some foreknowledge of image phantom type, this knowledge is not relevant at the initial stage of analysis beyond choosing what type of analysis is to be performed. Therefore, the requirement to choose the phantom type limits totally automated systems where many different image types may be present.

Unfortunately, current systems require the user to identify a phantom type and do not allow for quickly and efficiently conduct medical imaging quality assurance by effectively removing the requirement to identify a phantom type; current systems do not allow the user to move directly from loading an image to obtaining analysis results. Further, current systems have limited if any capabilities for automated analysis of multiple images in batch form.

DETAILED DESCRIPTION

Introduction

Disclosed herein are systems and methods for determining a type of medical imaging phantom present in an image, thereby allowing for relatively quick and efficient analysis of said image, e.g., by medical imaging quality assurance software. Advanced and novel image recognition techniques are used to provide the classification or type of a given phantom image. For example, classification of an image according to a type of imaging phantom and/or an analysis to be performed may be accomplished by using image data and possibly also image metadata, e.g., tags included in an image file or a separate file associated with the image according to the DICOM (Digital Imaging and Communications in Medicine) standard. Further, the disclosed systems and methods include dynamically self-optimizing recognition of individual phantom image types, as well as overall accuracy of image classification. Such self-optimization features advantageously provide accuracy and flexibility for future extension and addition of new phantom types.

Features of an exemplary system may include, without limitation:

Recognition and classification of images by using a cascading series of configurable machine learning and/or deterministic classifiers arranged in a hierarchical tree structure including general phantom families at a higher level and specific phantoms and specific parts of the phantom (e.g., slice in a CT phantom) at lower levels;

Configurability and expansibility to handle updated classification models and new phantoms;

A mechanism to provide system machine learning modules to remote clients via a network;

A mechanism to provide image attributes from clients to a remote classifier server or the like via a network to enable the system to continually improve its discrimination.

Exemplary System Elements

Figure 1:
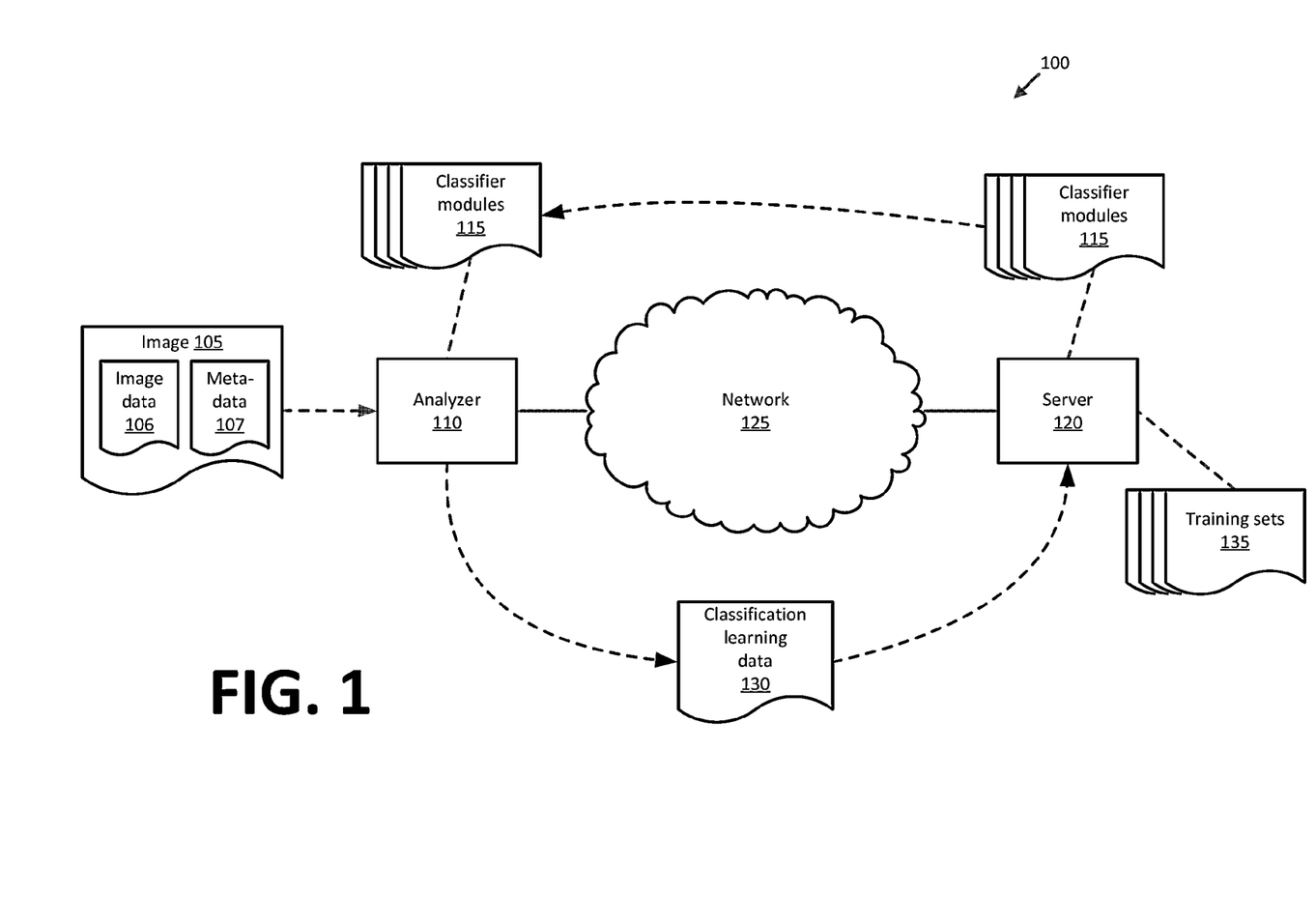
FIG. 1 is a block diagram of an exemplary phantom image classification system.

FIG. 1 is a block diagram of an exemplary classification system 100. An image 105 generated by a medical imaging device (not shown) is generally provided to an analyzer 110, which in an exemplary implementation includes a computing device having a processor and a memory, the memory having instructions stored thereon executable by the processor for classifying and/or analyzing the image 105. Such instructions may include one or more classification modules 115, which may be downloaded to the analyzer 110 from a remote server 120 via a network 125. Upon completion of an image 105 analysis, the analyzer 110 may provide classification learning data 130 to the server 120, e.g., via the network 125.

An image 105 may be generated using various types of phantoms with various types of medical imaging systems, e.g., a computed tomography (CT) scanner, and magnetic resonance imaging (MRI) system, etc. The image 105 generally includes image data 106, e.g., data specifying pixel locations, intensities, etc., in a known format such as DICOM, JPEG, GIF, PNG, etc., as well as image metadata 107, e.g., DICOM tags.

The analyzer 110 may include any computing device capable of performing operations described herein. For example, the analyzer 110 may be a general-purpose computer running a conventional operating system such as Windows, UNIX, Linux, etc. As mentioned above, the analyzer 110 includes instructions for classifying images 105. The system 100 may include multiple analyzers 110, although only one is shown in FIG. 1. Further, a memory of the analyzer 110 may include one or more classification modules 115 for use in classifying images 105.

Figure 5:
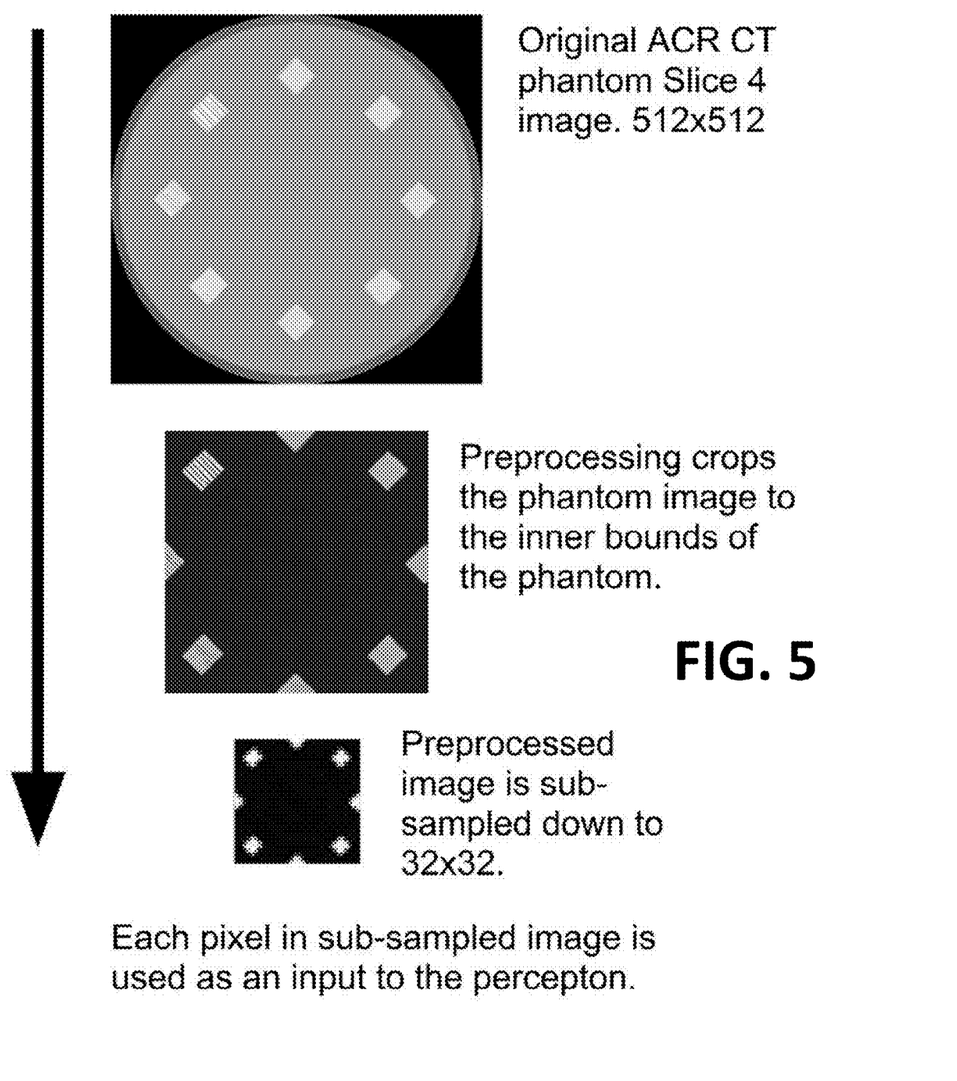
FIG. 5 is block diagram illustrating inputs to a perceptron as individual pixel values of the preprocessed and sub-sampled phantom image.

A classification module 115 may include instructions for deterministic and/or probabilistic classifications of images 105. For example, a classification module 115 may include instructions for deterministically classifying images 105 according to DICOM tags. Further, a classification module 115 may include instructions for probabilistically classifying images 105 using machine learning algorithms, e.g., neural network pattern recognition techniques, etc. In one exemplary implementation, a default configuration of a classifier includes single hidden layer multi-layer perceptrons, with 1024 input neurons and 72 hidden neurons. As illustrated in FIG. 5, inputs to a perceptron are individual pixel values of the preprocessed and subsampled phantom image 105. In addition to neural networks, machine learning techniques could be employed in a classifier 115, e.g., Support Vector Machines or various approaches to clustering for use in the classifications.

The server 120 may likewise include any computing device capable of performing operations herein, including one or more general-purpose computers running Windows, UNIX, Linux, etc. The server 120 may store one or more classification modules 115 that may be provided to analyzer 110, e.g., via the network 125. A classification module 115 may be updated or modified according to classification learning data 130 received from an analyzer 110.

The network 125 represents one or more mechanisms for providing communications between computing devices such as included in the analyzer 110, server 120, etc., including, for example, classification learning data 130 and classification modules 115. Accordingly, the network 120 may be one or more of various wired or wireless communication mechanisms, including any desired combination of wired (e.g., cable and fiber) and/or wireless (e.g., cellular, wireless, satellite, microwave, and radio frequency) communication mechanisms and any desired network topology (or topologies when multiple communication mechanisms are utilized). Exemplary communication networks include wireless communication networks, local area networks (LAN) and/or wide area networks (WAN), including the Internet, providing data communication services.

In general, classification learning data 130 may include pre-processed and/or sub-sampled phantom image 105 data along with a classification determined either by analyzer 110 in relation to a preset threshold value (e.g., 95% probability of being correct) or, in an exemplary implementation, by user input should the analyzer 110 not be able to accurately identify an image 105 to a predetermined likelihood of accuracy.

Training sets 135 may include classification learning data 130 from one or more analyzers 110 (and advantageously generally includes classification learning data 130 from a plurality of analyzers 110). That is, training sets 135 are stored in a data store included in or accessible to the server 120, and are used to periodically retrain machine learning classifiers 115, providing increases in machine learning classifier 115 accuracy.

Analyzer Components

Figure 2:
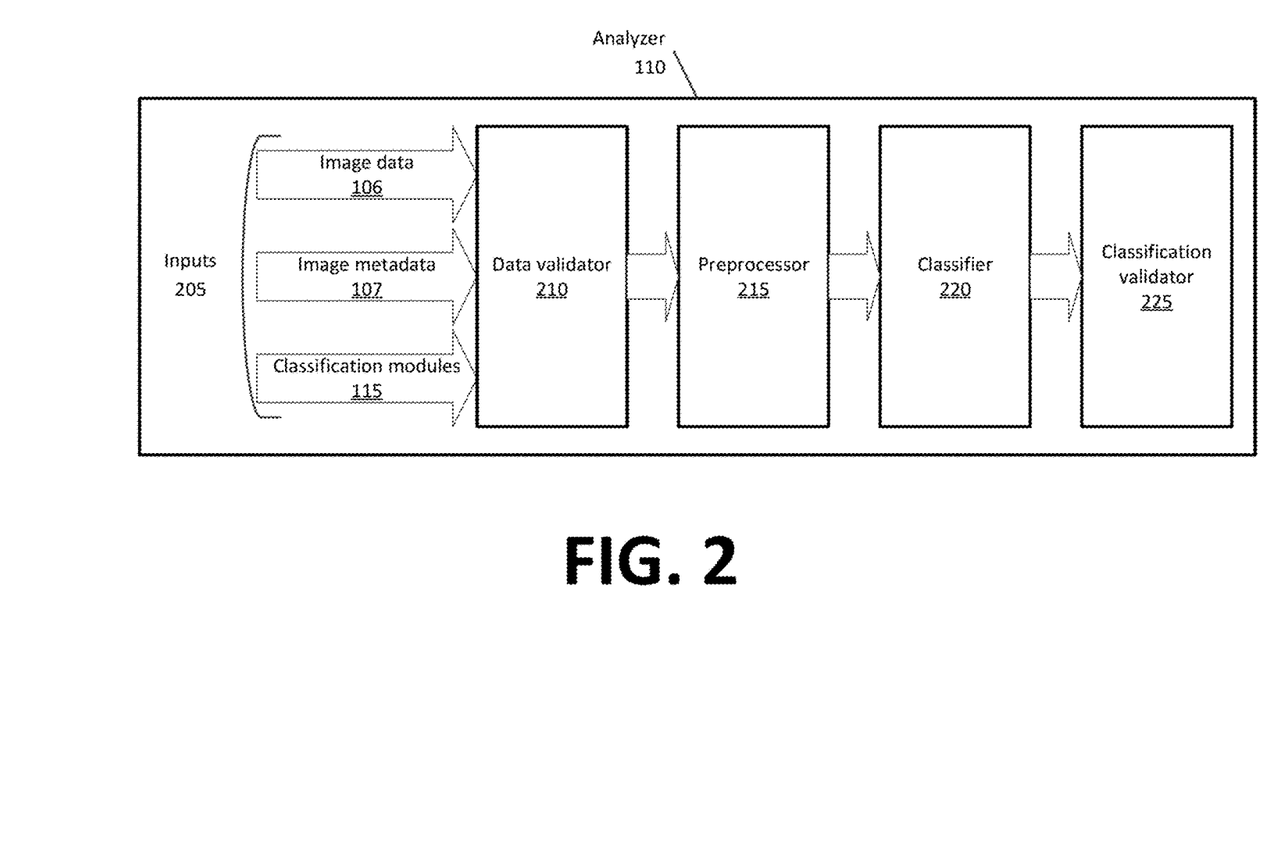
FIG. 2 is a block diagram illustrating components of an image analyzer.

FIG. 2 is a block diagram illustrating components of the analyzer 110. In general, inputs 205 to the analyzer 110 may include image data 106, image metadata 107, and/or one or more classification modules 115.

A validation module 210 may be included in the analyzer 110 to verify that input data 205 meets requirements of a classification module 115 being used to analyze image data 106 and/or metadata 107. In one exemplary implementation, validation criteria are included with a classification module 115.

If input data 205 is validated, data may be provided to a preprocessor 215. A classification module 115 generally also includes pre-processing requirements, if any. An advantage of including pre-processing requirements in the classification module 115 is that a classification module 115 may include pre-processing that is tailored to be highly accurate for specific families and/or types of phantom image data, thereby providing data likely or most likely to be best suited for a particular classification module 115. Examples of pre-processing routines include, without limitation, selecting a specific region of interest from an image 105, performing pre-defined filtering or other transformations on a raw image 105, extracting certain information from the image 105, e.g., from image data 106 and/or metadata 107, and/or performing predetermined calculations based on machine learning data and/or associated metadata included in the classification module 115.

Once inputs 205 are validated and pre-processed, they may be provided to a classifier 220. The classifier 220 generally includes instructions for applying a provided classification module 115 to image data 106 and/or image metadata 107. As mentioned above, the classifier 220 may include instructions for performing classifications by a variety of mechanisms, e.g., ranging from deterministic analysis of metadata 107 to neural network passed pattern recognition procedures. In general, as explained further below, the classifier 220 analyzes an image, including attempting image recognition, 105 by applying multiple classification modules 115 in a specified order to some or all of the image data 106 and/or metadata 107.

Output of the classifier 220 is generally provided to a classification validator 225, which compares the classifier 220 output to configurable validation parameters and thresholds to determine whether a classification provided by the classifier 220 may be considered valid.

Classification Module Search Tree

Figure 3:
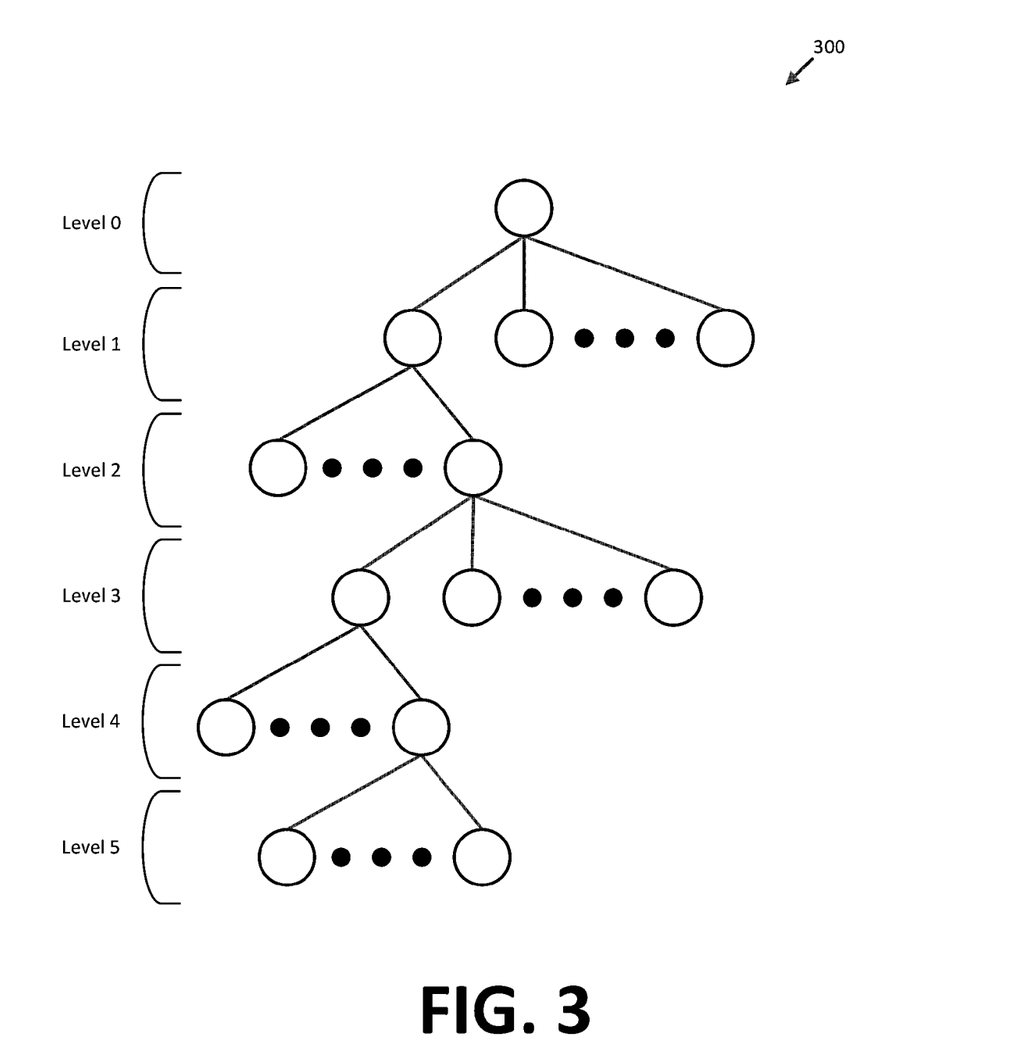
FIG. 3 illustrates an exemplary classification search tree.
Figure 4:
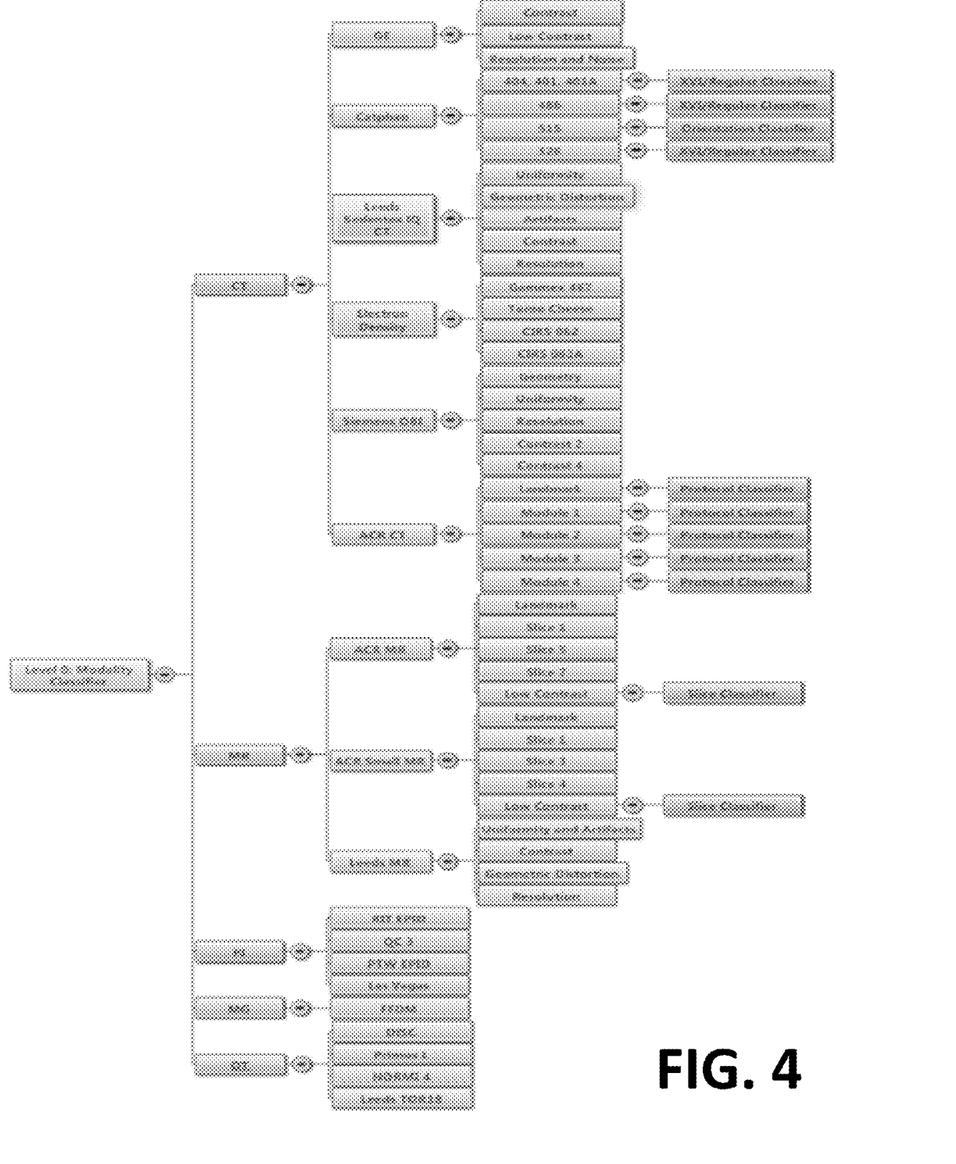
FIG. 4 provides an illustration of an actual search tree in an exemplary implementation.

As mentioned above, the classifier 220 may apply multiple classification modules 115 in a specified order to image 105. For example, in an exemplary implementation, classification modules 115 are arranged into a search tree 300 such as is illustrated in FIG. 3. A goal of the tree 300 is to provide a sequence of classifications of an image 105 that move from a coarse granularity, e.g., recognizing a general image 105 family, to finer and finer levels of granularity, e.g., identifying specific devices or even image slices. FIG. 4 provides an illustration of an actual search tree 400 in an exemplary implementation.

Accordingly, the tree 300 may include a Level 0 that classifies images 105 at a coarsest level of granularity. The Level 0 node is the root node of the tree 300, and hence the only node at that level. Unlike most if not all other nodes in the tree 300, the Level 0 node represents a single classification module 115 rather than a set of a plurality of classification modules 115. In an exemplary implementation, the Level 0 node utilizes a deterministic classification module 115 that analyzes a DICOM "modality" tag in image 105 metadata 107 to determine an image 105 family, e.g., MR (magnetic resonance), CT (computed tomography), MG (mammography), PI (portal imager), or OT (other), etc.

In this exemplary implementation, Level 1 of the tree 300 may include nodes representing each of the image 105 families that may be identified at Level 0. Accordingly, each Level 1 node generally includes one or more classification modules 115 that use a combination of the phantom image data 106 and also metadata 107 such as DICOM tag information to identify a phantom family to which a given phantom image 105 belongs. A phantom family is defined typically as a single physical phantom with multiple slices or areas of interest that each receive separate analysis, e.g., a collection of images 105 taken at different depths though the same phantom, or as a group of phantoms that share a similar appearance or other characteristics (usually because they are manufactured for the same testing purpose or to a common specification or standard). For example, the ACR CT phantom requires four distinct slice images 105 to be acquired from the single ACR CT QA Phantom. Each of these images 105 are members of the same ACR CT phantom family and as such generally share basic properties of the phantom itself.

Each classification module 115 is generally custom-built for each node in the tree 300, e.g., in the case of Level 1 nodes, classification modules 115 for the node are designed to yield more accurate classifications given the already-determined type of general medical imaging device the image came from, e.g., to narrow a determination of general type in the Level 0 node to a determination of image 105 family in the Level 1 node. Classification modules 115 in Level 1 nodes potentially also include basic machine learning algorithms to provide classification on facets of the image data such as overall phantom area or image uniformity.

Levels 0, 1, and 2 are sometimes referred to as "primary layers" of the tree 300 because, in this exemplary implementation, these levels of the tree 300 are generally performed for all images 105. The third and final primary layer, Level 2 of the tree 300, includes classification modules 115 that operate principally on the phantom image data 106 (as opposed to metadata 107). Like the classification modules 115 included in Level 1 nodes, classification modules 115 included in Level 2 nodes generally rely on machine learning algorithms for image recognition. As with Level 1, the implementation of each of these classification modules 115 is dependent on its specific purpose, i.e., each sub-classifier is typically optimized to deal with the type of image 105 passed to it from the previous layer of the search tree 300.

Generally, each family of phantom images 105 is represented in a respective Level 2 node by an aggregation of classification modules 115. Each such aggregation generally includes one classification module 115 for each type of phantom image within the image 105 family passed to the Level 2 node. Each of these specific classification modules 115 uses machine learning algorithms to determine a rough probability that a given image 105 is of the specific phantom type. In one example, classification of CT images 105 into specific phantoms and phantom families includes calculating an area of the phantom using a thresholding technique and the pixel size metadata to obtain inputs to a neural network classifier 115.

The default machine learning algorithm used for the classification modules 115 at Level 2 in this exemplary implementation is a set of single hidden layer multi-layer perceptrons. A single classification module 115 is used for each phantom image 105 type within a phantom image 105 family so that, in the event that the machine learning algorithms do not return a classification with a satisfactory level of accuracy, the sub-classifier aggregator can then return a list of likely candidates instead of just one potentially wrong one.

Using the hierarchal search tree 300 with its three principal Levels 0-2 of classification, a depth-first search algorithm is then used to walk through the tree and return overall potential classifications of a given phantom image 105. Because at least some nodes of the tree 300 use machine learning algorithms, which can never be assured of complete accuracy, the analyzer 110 generally compares the approximate probabilities of the most likely classifications for each individual image 105 to an overall threshold value assigned to the relevant family of phantom images 105. For instance, the analyzer 110 could be configured to accept any classification with an approximate probability of correct classification of over 95%. In the cases where no classifications or several classifications reach this threshold, the system in an exemplary implementation is required to ask the user for a decision as to the correct classification of the image. That decision is then recorded so that the machine learning algorithms can be further refined to increase the accuracy of classification.

Level 2 brings the classification to a physical phantom level. Level 3 accommodates phantoms that require further physical analysis, and Level 3 classifiers 115 may be used to return specific values to Level 2 classifiers 115, i.e., such values are used in Level 2 classifiers 115 to determine the overall classification of an image 105 within a given family. That is, Level 2 classifiers determine what the given image is based on all the roughly probabilistic values returned to it from all of its Level 3 classifiers. For example, in modalities that are 3D (three-dimensional) in nature (e.g., CT, MR) there are typically a number of slices (separate images) that are analyzed for different things. Accordingly, once a determination has been made of the overall phantom in Level 2, it remains necessary to sub-classify (e.g., as done in Level 3) an image 105 into slices for a 3D phantom. Accordingly, in an exemplary implementation, there is a single Level 3 classifier 115 for each of the general classifications, e.g., slices, designed to determine the probability that the given image 105 is of that specific type. For example, a "Slice01" classifier 115 is designed to specify only a probability that a given image 105 is of the type "slice 1." As an example of a 3D image, the ACR CT phantom has five slices (or "modules" in ACR CT parlance) to be analyzed: 0: Slice thickness calculation; 1: Material Value; 2: Low contrast and contrast to noise measurements; 3: Uniformity; and 4: Resolution.

For 2D phantoms, such as are used for analyzing planar image quality, the sub-classification of Level 3 is typically not required as all the analysis is done on a single image 105.

In general, Level 4 to Level N classifiers may be included in the tree 300 to provide flexibility. For example, should preceding levels of classification not be sufficient to produce a fine enough level of granularity in classifying an image 105, more layers can be introduced where needed. For instance, in ACR CT classification, each image has a type of imaging protocol which was conducted. Because this information is required for the eventual QA analysis of the image, the images not only need to be classified correctly as, e.g., "Slice 1," but also as "Adult—Abdomen" for the protocol.

Accordingly, in an exemplary implementation, Level 4 includes classification modules 115 that classify images 105 according to a protocol, i.e., a specific imaging device setup. It will be understood that, in some cases, pass-fail specifications are different for different protocols. Protocol determination is generally deterministic based on the image 105 metadata 107, e.g., kV and mA settings, although there are cases, including as noted in the below examples, where probabilistic determinations may also be used. Examples of Level 4 classifications in this exemplary implementation include the following:

The ACR CT analysis procedure requires the user to image the phantom with typical machine settings used for Adult Head, Adult Abdomen, Pediatric Head and Pediatric Abdomen (settings are adjusted to account for the smaller cross profile in pediatric cases to minimize radiation dose exposure);

Catphan images: On three of the Catphan slices the particular analysis routine employed depends on the provenance of the image 105. For example, an Elekta iView machine required specialized analysis routines that are used in place of the more generalized Catphan analyses. Typically, determining image 105 provenance would be determined by image 105 metadata 107, as noted above, although analysis of certain image 105 characteristics (pixel value levels etc.) may be employed for this particular Level 4 determination.

Slice Classifier: Some images 105 that need to be distinguished are very similar to each other. An example includes low contrast slices on the ACR MR phantom. It is fairly easy to determine that the image 105 is a low contrast slice, but to determine exactly which low contrast slice may require analysis using machine learning algorithms as well as examination of the image 105 metadata 107.

Level 5, shown with respect to the exemplary implementation illustrated herein, is optional. In the presently-illustrated Level 5 analysis, images 105 may be rotated or mirrored from the orientation generally required for analysis. Typically such translation occurs on 3D phantoms due to changing the scan direction (causes mirroring) or assembling parts of the phantom in the wrong orientation (rotation). Similar issues may occur in 2D phantoms where the user positions the phantom in an inconsistent rotation in the imaging equipment. Accordingly, analyzer 110 may use deterministic routines for analyzing image 105 orientation; in some cases, machine learning algorithms may be more robust and adaptable for this purpose.

Optmization

The use of approaches customized in each of the individual single classification modules 115 to an image family, type, etc., being analyzed, allows the system 100 to dynamically optimize its results as more information becomes available when a phantom image 105 is analyzed. This is achieved in each node of the tree 300 by storing an anonymized copy of the pre-processed and/or sub-sampled phantom image 105 data along with its correct classification, as determined either by the classifier's probabilities in relation to a preset threshold value or, in an exemplary implementation, by user input should the analyzer 110 not be able to accurately identify an image. This information is then provided as classification learning data 130 to the remote server 120 in a series of training sets 135, with a single training set 135 corresponding to a classification module 115.

The models that machine learning algorithms in classification modules 115, for instance the topology and weight values which allow the default multilayer perceptron to work, may be periodically retrained using whatever standard algorithms machine learning practices dictate. The action of retraining these models is triggered either by a set period of time elapsing since the last retraining was attempted, or by a sufficient amount of new data being added to the training set associated with a specific machine learning model. By using training sets that are gradually increasing in both size and diversity, the machine learning algorithms on which the image 105 classification is based, i.e., that are included in classification modules 115, can be selectively updated for better accuracy; that is, rather than updating an entire classification model such as represented by a tree 300, in the present system 100 classification modules 115 corresponding to particular nodes in the tree 300, i.e., selected portions of the classification model, may be updated. Each time a new model is trained; its accuracy is statistically evaluated and compared to the model which is currently in use in a respective classification module 115, if a sufficient positive change in accuracy is recorded, then the current model is archived and the new model takes its place. A process for training new models is discussed below with respect to FIG. 7.

As such, the system 100 is designed to allow for repeated updating of any given model which corresponds to a specific sub-classifier component based on increases in that machine learning model's accuracy. In this way the accuracy of the overall system 100, and analyzers 110 therein, can be gradually increased as sub-classifier components, i.e., classification modules 115, fulfill their role better. The fact that the overall system can actively update its discrete machine learning models allows the system to self-optimize itself based on all current information over a period of time, achieved by altering only the sub-classifiers which are ill performing while maintaining and ensuring the integrity of the rest of the classification system.

Exemplary Process Flows

Figure 6:
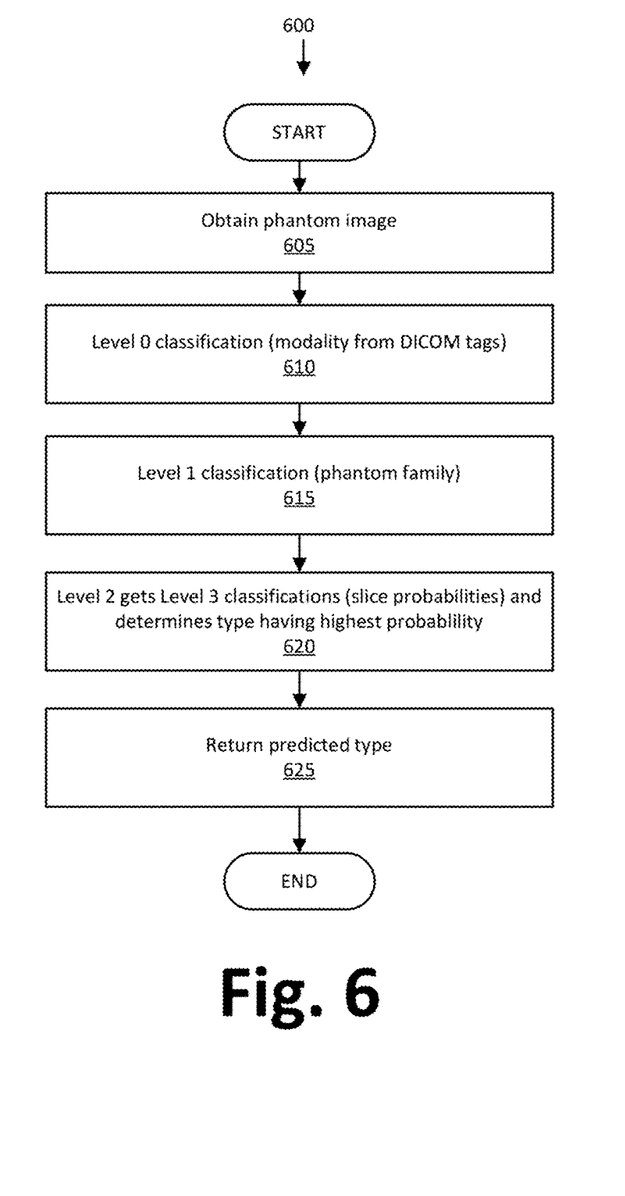
FIG. 6 is an exemplary process flow of determining an image type.

FIG. 6 illustrates a process 600 of determining an image type where an image 105 turns out to be predicted to belong to a multi-slice modality such as CT or MRI. The process 600 begins in a block 605, in which the analyzer 110 obtains an image 105, e.g., a file generated by an imaging device.

In the subsequent blocks of the process 600 described below, a series of a plurality of classifiers 115 is used to predict the type of the image 105. The series of classifications typically moves from general classifications to specific classifications.

For example, in a block 610 which may follow the block 605, a Level 0 (or the first level of) classification is performed such as described above, broadly classifying the image 105; e.g., an image modality is determined from some image parameters (such as image size, image file extension, image file name, etc.), embedded image tag (such as DICOM tags or other metadata 107), or characteristic of the image 105 itself (such as the probability of an image slice type). For instance, in an exemplary implementation, the Level 0 classification might be chosen to be based on metadata 107 such as one or more (or some Boolean combination or regular expression parsing) of the many possible DICOM or embedded image tags. The modality of the image 105, in this example, may be used because it is one of the most general classifications that can occur on any image 105 generated by an imaging device, and, if initially determined, can significantly prune possible pathways in the classification tree 300.

Next, in a block 615, a next level classification is performed, which is generally more specific than the preceding classification. For example, as discussed above, a Level 1 classifier 115 may use a combination of use of image 105 parameters such as image data 106 and metadata 107. For example, image qualities such as dimensions, area, uniformity of pixels, etc., may be taken into account. For purposes of the exemplary process 600, it is assumed that a phantom family is identified in the block 615.

Accordingly, next, in a block 620, because in the present example phantom family image 105 will include multiple image slices, a Level 2 classifier 115 calls upon Level 3 classifiers 115 to identify probabilities, for each of the possible slice types, that the image 105 is that slice type. Each Level 3 classifier 115 returns a probability to the Level 2 classifier 115. The Level 2 classifier 115 for example, in turn identifies the slice type having the highest probability of being associated with the image 105.

Instructions included in, or executed in conjunction with, the Level 3 classifiers 115 may include instructions for preprocessing and sub-sampling the image 105. For example, an "inner crop" of an image 105 may be defined, i.e., preprocessing may include excluding pixels in image data 106 near an image 105 edge or a particular object in the image. Further, within that inner crop, sub-sampling may be performed to select a subset of pixels in the cropped image data 106, e.g., in an exemplary implementation sub-sampling may be performed to yield a smaller set of pixels of image data 106, upon which the classifier 115 then operates, e.g., in an exemplary implementation sub-sampling is performed to yield a 32 pixel by 32 pixel set of image data 106, upon which the classifier 115 then operates.

Accordingly, these lower levels 2 and 3 in the tree 300 are used in this exemplary process 600 to further refine the classification of a type of image 105 so as to become more specific with each successive layer. Moreover, in this example, layers working in conjunction with one another to provide more specific classification of an image 105 generated from an imaging device. While Levels 2 and 3 of the exemplary process utilize probabilistic reasoning, the process of recurrently classifying an image 105 with an increasing degree of specificity does not require use of probabilistic determination. Further, it should be noted that if multiple image slices were not used in the phantom, the block 620 may be skipped. Alternatively, even in cases where there are not multiple slices, the block 620 may nonetheless be needed if several different types of phantoms may generate, similar images 105 and so require a classifier 115 to discriminate between these similar images 105. In general, a given classifier 115 may or may not be used depending upon the need.

Classification performed in the process 600 as described through the block 620 may still be inadequate for determining a type of image 105 with sufficient accuracy. In general, determining whether a classification is sufficiently accurate may be performed in a conventional manner. For example, it is known in statistical analysis to set "alpha" and "beta" levels, e.g., in the present context, weighing a degree of desired certainty (i.e., probability) that a classification is correct (alpha), against a risk of rejecting a phantom that was actually correctly classified (beta). Further, accuracy thresholds could be adjusted based on the performance of a particular model as well as particular user requirements. For instance, in a situation where a model does not often return more than a 55% certainty of classification, but does so reliably and objectively accurately (as determined by the ROC curve for example), an accuracy threshold might be set to be 51% or above. In general, this type strict threshold adjustment is employed only as warranted.

Where a classification is insufficiently accurate, more levels of classifiers 115 may be utilized to achieve a high enough certainty that the correct image type has been identified. For example, further levels of the tree 300 may employ classifiers focusing on various image 105 feature sets such as described below with respect to the process 800 of FIG. 8. At some point, if the probability is still too low or the analyzer 110 is inadequately certain of its classification, the image 105 may be returned to the user for manual classification which may result in the addition of a new data type.

Next, in a block 625, the analyzer 110 returns to a user the image 100 identification, i.e., including the slice type, determined in the block 620.

Following the block 625, the process 600 ends.

Figure 7:
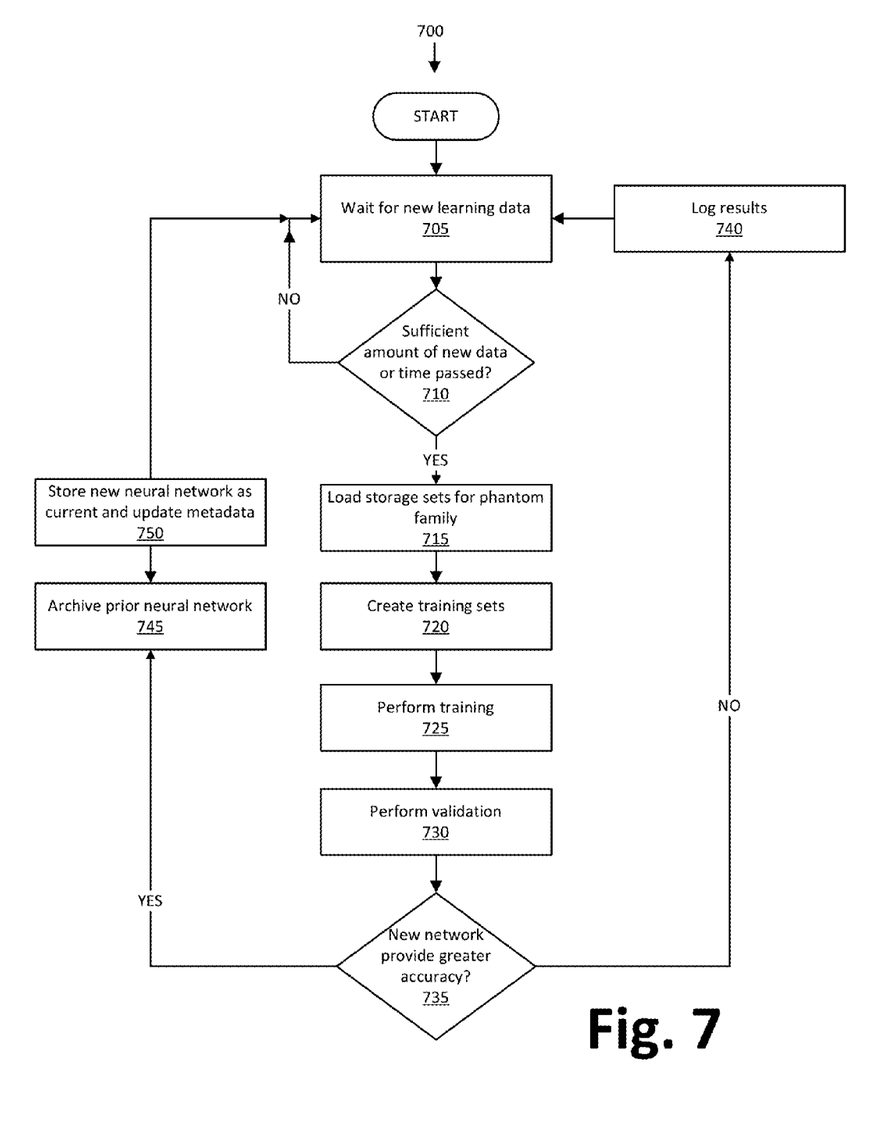
FIG. 7 includes an exemplary process for training and/or updating a neural network.

FIG. 7 illustrates an exemplary process 700 for the system 100 to self-optimize classifiers 115, neural networks in the present example, although other machine learning techniques are also possible.

The process 700 begins in a block 705, in which the server 120 waits for a new set or sets of classification learning data 130.

Next, in the block 710, the server 120 determines whether it has received an amount of classification learning data 130 from one or more analyzers 110 in excess of a threshold predetermined to represent an amount of classification learning data 130 sufficient to perform a neural network training exercise. Alternatively or additionally, the server 120 may determine whether a predetermined amount of time has passed. If no time or data volume threshold is met, the process 700 may return to the block 705. Otherwise, the process 700 generally proceeds to a block 715.

In the block 715, the server 120 loads existing neural network models used in classifiers 115 for a phantom family indicated by the classification learning data 130 received in the block 705. For example, if the classification learning data 130 is identified as relating to an ACR CT phantom, then the server 120 could load neural network models relating to identifying slices 1-4 of such a phantom.

Next, in a block 720, the server 120 creates a training set 135 for each of the neural network models loaded in the block 715. That is, the classification learning data 130 may be used to set desired values for machine learning with respect to each of the neural network models.

Figure 8:
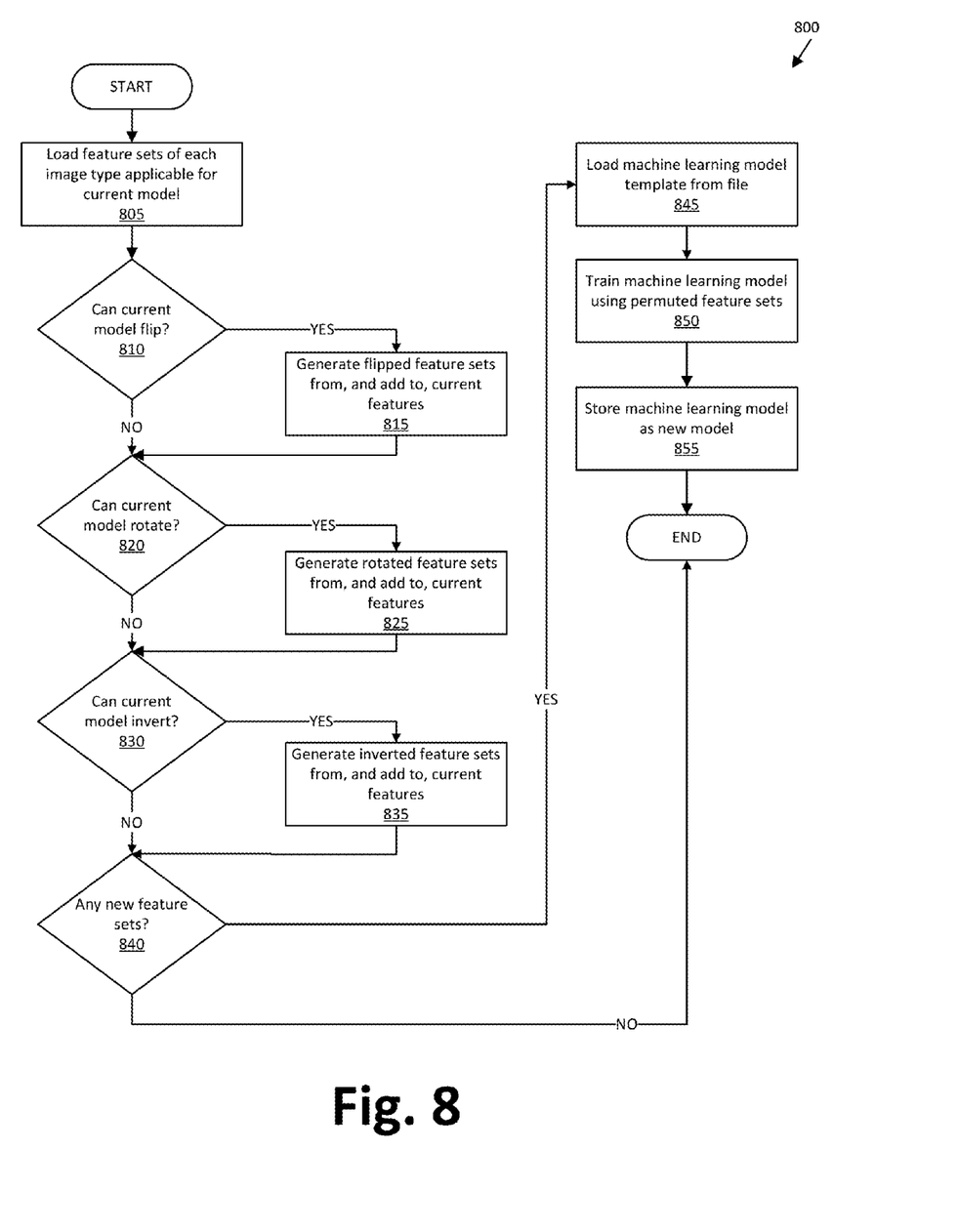
FIG. 8 illustrates an exemplary process for generating and using training sets pertaining to one or more feature sets of an image.

Next, in a block 725, the server 120 performs training with respect to each of the training sets 135. FIG. 8, discussed below, illustrates an exemplary process 800 including further details of generating and using training sets 135 as discussed with respect to the blocks 715-725.

Next, in a block 730, the server 120 validates each network trained in the block 725, e.g., using ten-fold cross validation or some other validation technique. For example, if ten-fold cross validation is used, the server 120 may store a statistically-based accuracy measure from the validation, along with a receiver operating characteristics (ROC) curve of the validation's performance to measure the sensitivity and specificity of the classifier 115.

Next, in a block 735, after performing the validation of block 730, the server 120 determines whether each classifier 115, e.g., network, trained in the block 725 provides greater accuracy than a currently-used model, e.g., a predecessor neural network to a neural network now being evaluated as part of the process 700. For example, if 10-fold cross validation has been used, the server 120 could compare the currently-used model's ROC and accuracy with the area under the ROC curve and accuracy, determined as described above with respect to the block 730, of the new model being evaluated as part of the process 700. For any network not providing greater ROC and accuracy, results are logged in a block 740, and the process 700 returns to the block 705. However, for any network providing greater accuracy, the process 700 proceeds to a block 745.

In the block 745, a previous, and now determined to be less-accurate, neural network is stored in an archive.

Next, in a block 750, a classifier 115, e.g., a new neural network is stored as being current for a respective classifier module 115. Further, mechanisms are generally employed to insure that analyzers 110 are updated with the most current classifiers 115. For example, a table of metadata or the like may be updated by the server 120 to include the new classifier 115, such metadata listing all available classifiers 115 according to image 105 types, etc. Further, the metadata, or new classifiers 115, could be distributed to analyzers 110 via the network 125, e.g., pushed on a regular basis, in response to queries for new classifiers 115 (for example, an analyzer could be configured to check for new classifiers 115 on start-up, at predetermined intervals, etc.), etc.

Following the block 750, the process 700 returns to the block 705. Of course, although not explicitly illustrated in FIG. 7, it should be understood that the process 700 could be terminated via a variety of mechanisms. For example, the server 120 could be powered off, a software application executing the process 700 could be terminated or configured to run only for a predetermined period of time or at predetermined times, etc.

FIG. 8 illustrates an exemplary process 800 for generating and using training sets 135 pertaining to one or more feature sets of an image 105. Feature sets are also sometimes referred to as image 105 permutations. For example, images 105 can include feature sets relating to an image 105 being flipped, rotated, and/or inverted, etc. For purposes of the present example, a flipped image 105 is one that has been reversed along a horizontal and/or vertical axis, a rotated image 105 is one that has been turned, i.e., rotated, with respect to some point, and an inverted image 105 is one where pixel values may be represented as the inverse of the actual values, akin to a photographic negative.

The process 800 may be initiated following completion of the process 700, e.g., after a new classifier 115, e.g., neural network, is stored as described concerning the block 750. In any case, the process 800 begins in a block 805, in which a model, e.g., a neural network, to be trained is loaded by the server 120, such as is described above with respect to the block 715 of the process 700, along with one or more feature sets applicable to the model, e.g., feature sets applicable to an image 105 being flipped, rotated, and/or inverted, etc.

Next, in a block 810, the server 120 determines whether the current model can include a flipped feature set. For example, the current model may pertain to determining whether an image 105 was generated by a device not capable of generating a flipped image, or the device and image types to which the current model pertains may be associated with a flipped image. If a flipped feature set is possible, then a block 815 is executed next. Otherwise, the process 800 proceeds to a block 820.

In the block 815, the server 120 analyzes current image 105 features included in the model being analyzed, and generates a flipped feature set therefrom, that is, determines features for a flipped image 105 based on the current image 105 features. The server 120 then adds the flipped features to a set of current image 105 features, e.g., parameters such as discussed above, e.g., size, pixel density, etc., for the model.

In a block 820, the server 120 determines whether the current model can include a rotated feature set. If so, a block 825 is executed next. Otherwise, the process 800 proceeds to a block 830.

In the block 825, the server 120 analyzes current image 105 features included in the model being analyzed, and generates a rotated feature set therefrom, that is, determines features for a rotated image 105 based on the current image 105 features. The server 120 then adds the rotated features to a set of current image 105 features for the model. Following the block 825, the process 800 proceeds to a block 830.

In a block 830, the server 120 determines whether the current model can include an inverted feature set. If so, a block 835 is executed next. Otherwise, the process 800 proceeds to a block 840.

In the block 835, the server 120 analyzes current image 105 features included in the model being analyzed, and generates an inverted feature set therefrom, that is, determines features for an inverted image 105 based on the current image 105 features. The server 120 then adds the inverted features to a set of current image 105 features for the model. Following the block 835, the process 800 proceeds to the block 840.

In the block 840, the server 120 determines whether any new feature sets have been added to the feature set associated with the current model, e.g., whether any of a block 815, 825, and/or 835 have been executed. If new feature sets have not been added, then the process 800 ends. Otherwise, the process 800 proceeds to a block 845.

In the block 845, the server 120 loads a machine learning model template, e.g., from a file, for use with a training set 135 for the model being evaluated.

Next, in a block 850, the server 120, using the model template and one or more new feature sets created, for example, as described with respect to the block 815, 825, 835, creates and uses a training set 135 to generate a new model, e.g., a new classifier module 115.

Next, in a block 855, the model generated as described with respect to the block 850 may be stored by the server 120. Further, the model may be validated as described above with respect to the process 700.

Following the block 855, the process 800 ends. Advantageously, the process 800 allows for classifiers 115 to be selectively updated and/or optimized based on new classification learning data 130 related to images 105 having different feature sets. Further, it is possible to update a model with respect to one, some, or all feature sets that may be associated with a type of image 105. For example, server 120 could conduct multiple iterations of the process 802 generate a set of classifiers 115, wherein each classifier 115 would pertain to a particular combination of one or more feature sets. Accordingly, to continue the example, classifiers 115 could be available for a particular image 105 type if the image was one or more of flipped, rotated, and inverted.

CONCLUSION

Computing devices such as those discussed herein generally each include instructions executable by one or more computing devices such as those identified above, and for carrying out blocks or steps of processes described above. For example, process blocks discussed above may be embodied as computer-executable instructions.

Computer-executable instructions may be compiled or interpreted from computer programs created using a variety of programming languages and/or technologies, including, without limitation, and either alone or in combination, Java™, C, C++, Visual Basic, Java Script, Perl, HTML, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media. A file in a computing device is generally a collection of data stored on a computer readable medium, such as a storage medium, a random access memory, etc.

A computer-readable medium includes any medium that participates in providing data (e.g., instructions), which may be read by a computer. Such a medium may take many forms, including, but not limited to, non-volatile media, volatile media, etc. Non-volatile media include, for example, optical or magnetic disks and other persistent memory. Volatile media include dynamic random access memory (DRAM), which typically constitutes a main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

In the drawings, the same reference numbers indicate the same elements. Further, some or all of these elements could be changed. With regard to the media, processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A system, comprising a computing device that includes a processor and a memory, the memory storing instructions executable by the processor, the instructions including instructions for:
    using image metadata to perform a first sub-classification of an image, wherein the first sub-classification is deterministic;
    based in part on the deterministic first sub-classification, using a combination of image data of the image and the image metadata to perform a second sub-classification, and
    in a third sub-classification, based in part on the second sub-classification, using the image data to make a probabilistic classification of the image according to a likely phantom type.

2. The system of claim 1, wherein the image metadata includes DICOM tags.

3. The system of claim 1, wherein the second sub-classification identifies an image family.

4. The system of claim 1, wherein the image data includes information concerning at least a location and intensity of pixels in the image.

5. The system of claim 1, wherein a modality of the image represents a type of medical imaging device that produced the image.

6. The system of claim 1, the instructions further comprising instructions for providing output of the third sub-classification to a remote server for use in training data.

7. The system of claim 1, wherein at least one of the first sub-classification, the second the first sub-classification, and the third the first sub-classification are performed at least in part according to instructions downloaded to the computing device from a remote server.

8. A method, comprising:
    using image metadata to perform a first deterministic sub-classification of an image;
    based in part on the deterministic first sub-classification, using a combination of image data of the image and the image metadata to perform a second sub-classification, and
    in a third sub-classification, based in part on the second sub-classification, using the image data to make a probabilistic classification of the image according to a likely phantom type.

9. The method of claim 8, wherein the image metadata includes DICOM tags.

10. The method of claim 8, wherein the second sub-classification identifies an image family.

11. The method of claim 8, wherein the image data includes information concerning at least a location and intensity of pixels in the image.

12. The method of claim 8, wherein the a modality of the image represents a type of medical imaging device that produced the image.

13. The method of claim 8, further comprising providing output of the third sub-classification to a remote server for use in training data.

14. The method of claim 8, wherein at least one of the first sub-classification, the second the first sub-classification, and the third the first sub-classification are performed at least in part according to instructions downloaded from a remote server.

15. A system, comprising a computing device that includes a processor and a memory, the memory storing instructions executable by the processor, the instructions including instructions for:
    receiving, via a network, a set of image analysis data;
    identifying an image analysis model to be trained, using the image analysis data;
    determining that the image analysis model can include an image permutation; and
    training a new image analysis model including the image permutation and
    using the new image analysis model to predict a probability that an image relates to a specific phantom.

16. The system of claim 15, wherein the image analysis model is a neural network.

17. The system of claim 15, wherein the image permutation is at least one of a flipped feature, a rotated feature, and an inverted feature.

18. The system of claim 15, the instructions further including instructions for training the image analysis model not including the image permutation.

19. The system of claim 15, the instructions further including instructions for validating the new image analysis model.

* * * * *

UNITED STATES PATENT AND TRADEMARK OFFICE
CERTIFICATE OF CORRECTION

PATENT NO. : 9,466,012 B2
APPLICATION NO. : 13/952003
DATED : October 11, 2016
INVENTOR(S) : Daneil M. Ritt et al.

It is certified that error appears in the above-identified patent and that said Letters Patent is hereby corrected as shown below:

In the claims:

Column 14, in lines 8-9, replace "the second the first sub-classification, and the third the first sub-classification" with -- the second sub-classification, and the third sub-classification --

Column 14, in line 31, replace "wherein the a modality" with -- wherein a modality --

Column 14, in lines 38-39, replace "the second the first sub-classification, and the third the first sub-classification" with -- the second sub-classification, and the third sub-classification --

Signed and Sealed this
Twenty-ninth Day of November, 2016

Michelle K. Lee
*Director of the United States Patent and Trademark Office*